United States Patent
Li et al.

(10) Patent No.: US 8,304,582 B2
(45) Date of Patent: Nov. 6, 2012

(54) FLUIDIZED CATALYTIC PROCESS FOR PRODUCTION OF DIMETHYL ETHER FROM METHANOL

(75) Inventors: Zheng Li, Beijing (CN); Qiang Fu, Beijing (CN); Chaogang Xie, Beijing (CN); Minggang Li, Beijing (CN); Anguo Mao, Beijing (CN); Lisheng Li, Beijing (CN); Genquan Zhu, Beijing (CN); Fengmei Zhang, Beijing (CN); Yi bin Luo, Beijing (CN)

(73) Assignees: China Petroleum & Chemical Corporation, Beijing (CN); Research Institute of Petroleum Processing, Sinopec, Beijing (CN)

( * ) Notice: Subject to any disclaimer, the term of this patent is extended or adjusted under 35 U.S.C. 154(b) by 381 days.

(21) Appl. No.: 12/594,006

(22) PCT Filed: Mar. 27, 2008

(86) PCT No.: PCT/CN2008/000615
§ 371 (c)(1),
(2), (4) Date: Nov. 9, 2009

(87) PCT Pub. No.: WO2008/119251
PCT Pub. Date: Oct. 9, 2008

(65) Prior Publication Data
US 2010/0076227 A1 Mar. 25, 2010

(30) Foreign Application Priority Data
Mar. 30, 2007 (CN) .......................... 2007 1 0064974

(51) Int. Cl.
*C07C 41/09* (2006.01)
*C07C 43/04* (2006.01)
*F27B 15/08* (2006.01)

(52) U.S. Cl. ........................................ 568/698
(58) Field of Classification Search ................ None
See application file for complete search history.

(56) References Cited

U.S. PATENT DOCUMENTS

| | | | | |
|---|---|---|---|---|
| 4,071,573 A | * | 1/1978 | Owen et al. | 585/402 |
| 4,328,384 A | | 5/1982 | Daviduk et al. | |
| 4,404,414 A | * | 9/1983 | Penick et al. | 585/469 |
| 4,554,260 A | * | 11/1985 | Pieters et al. | 502/61 |
| 4,761,513 A | | 8/1988 | Steacy | |
| 2004/0034255 A1 | | 2/2004 | Shoji et al. | |

FOREIGN PATENT DOCUMENTS

| | | |
|---|---|---|
| CN | 1125216 A | 6/1996 |
| CN | 1180064 A | 4/1998 |
| CN | 1301686 A | 7/2001 |
| CN | 1368493 A | 9/2002 |
| WO | WO 2007/006238 A1 * | 1/2007 |

* cited by examiner

*Primary Examiner* — Rosalynd Keys
(74) *Attorney, Agent, or Firm* — Scully, Scott, Murphy & Presser, P.C.

(57) ABSTRACT

The present invention provides a fluidized catalytic process for production of dimethyl ether from methanol, wherein said process is carried out in a reactor in which the catalyst is in a fluidized state. Said process comprises the following steps of (1) feeding the methanol feedstock via two or more locations selected from the bottom, lower part, middle part and upper part of the reactor, contacting with the catalyst for preparation of dimethyl ether by methanol dehydration, carrying out the reaction of preparing dimethyl ether by methanol dehydration to obtain the reaction stream, separating said reaction stream to obtain a coked catalyst and a crude product primarily containing the target product, i.e. dimethyl ether; (2) totally or partially feeding the coked catalyst obtained in step (1) into a regenerator in a continuous or batch manner for regeneration via coke-burning, the regenerated catalyst being directly recycled to step (1) after being totally or partially cooled.

19 Claims, 2 Drawing Sheets

FLUIDIZED CATALYTIC PROCESS FOR PRODUCTION OF DIMETHYL ETHER FROM METHANOL

TECHNICAL FIELD

The present invention relates to a process for producing ether from alcohols, more specifically a fluidized catalytic process for production of dimethyl ether from methanol

BACKGROUND OF THE INVENTION

Dimethyl ether (DME) can be produced by one-step process and two-step process. The one-step process refers to one-step synthesis of dimethyl ether from the synthetic gas, and the two-step process refers to synthesis of methanol from the synthetic gas, and then preparation of dimethyl ether via dehydration.

The two-step process is carried out via two steps, i.e. synthesizing methanol from the synthetic gas, and then dehydrating methanol with the catalysis of an acid to prepare dimethyl ether. The two-step process for synthesis of dimethyl ether is the primary process for producing dimethyl ether at home and abroad. Said two-step process uses fine methanol as the feedstock, and has the advantages of less by-products of the dehydration reaction, high purity of dimethyl ether, mature technique, wide adaptability of the device, and simple posttreatment. Said two-step process can be directly used in a methanol factory, or other non-methanol factory having established public utilities. Generally, ZSM-5 molecular sieve comprising $\gamma Al_2O_3/SiO_2$ is used at home or abroad as the dehydration catalyst, wherein the reaction temperature is controlled at 280-340° C. and the pressure at 0.5 to 0.8 MPa. The single-pass conversion of methanol is from 70 to 85%; and the selectivity of dimethyl ether is greater than 98%.

CN1180064A discloses a process for producing dimethyl ether from methanol at a fairly low temperature (from 100 to 125° C.) and almost atmospheric pressure (from 0 to 0.05 MPa gauge pressure) in the presence of a new catalyst to produce a dimethyl ether gas.

CN1125216A discloses a process for producing dimethyl ether from methanol, comprising feeding methanol into the vaporization column to remove substances having a high boiling point and impurities, catalytically dehydrating in the presence of a composite solid acid catalyst in a multi-stage cold quenching reactor, then feeding the dehydrated product into a high performance package column for fractionation, and selecting different operation reflux ratios according to different requirements to produce a dimethyl ether product having a purity from 90 to 99.99%.

CN1368493A discloses a process for producing dimethyl ether by catalytically dehydrating methanol, and relates to a process for producing dimethyl ether by catalytic dehydration of methanol, wherein the dehydration is carried out in the presence of a solid acid catalyst containing $SO_4^{2-}$. In the catalyst, $SO_4^{2-}$ is preferably in an amount from 2 to 25 wt %. The preferred catalyst support is selected from the group consisting of $\gamma$—$Al_2O_3$, $\eta$—$Al_2O_3$ and $SiO_2$.

CN1301686A discloses a process for producing dimethyl ether by dehydrating methanol, comprising using sulfuric acid modified kaolin as a catalyst for the preparation of dimethyl ether via methanol dehydration.

US2004/0034255A1 discloses a process for producing dimethyl ether, which includes dehydrating methanol in vapor phase in the presence of an activated alumina catalyst having an average pore radius of 2.5 nm to 8.0 nm and having a sodium oxide content less than 0.07 wt %.

Said processes above primarily concern producing dimethyl ether by dehydrating methanol via catalysis with a composite solid acid, an acid-modified kaolin, an activated alumina, and the like. Moreover, a fixed bed reactor is mainly used therein. The resultant dimethyl ether is usually used as fine chemicals. In addition, said processes have a small scale of production and a higher production cost.

On the other side, the attempt of multipoint feeding has been carried out in various fixed bed methods or catalytic cracking methods. For example, U.S. Pat. No. 4,761,513 discloses a toluene alkylation method, comprising feeding the alkylation reagents from different sites of the fixed bed. In these methods, fairly big catalyst bed are needed to receive the reaction heat in order to prevent the potentially adverse effect of exothermic reaction on the product selectivity, resulting in a great increase of the device investment and operating cost. In addition, the reaction of producing dimethyl ether by dehydration of methanol is an exothermic reaction. Under the nearly adiabatic circumstance, the temperature of the catalyst bed layer gradually increases along with the proceedings of the reaction. If the reaction heat fails to be taken out or consumed timely, the pyrolytic reaction of methanol is prone to take place to produce much non-condensable gases, e.g. carbon oxides and hydrogen gas. Meanwhile, excessive high reaction temperature also results in the further dehydration of the resultant dimethyl ether to produce many low-carbon olefins, e.g. ethylene, propylene and butylene, so as to render notable decrease of the selectivity of dimethyl ether.

SUMMARY OF THE INVENTION

Thus the inventor seeks for a novel process for the preparation of dimethyl ether, which is suitable for large-scale production, has high methanol conversion and dimethyl ether selectivity, and can avoid deep reaction resulting in low-carbon olefins.

With extensive efforts and studies, the inventor invents a fluidized catalytic process for producing dimethyl ether by dehydration of methanol in gaseous phase on the basis of the prior art, so as to increase the methanol conversion and the selectivity of dimethyl ether.

The fluidized catalytic process for producing dimethyl ether from methanol in the present invention is carried out in a reactor in which the catalyst is in a fluidized state, comprising the following steps:

(1) feeding the methanol feedstock via two or more locations selected from the bottom, lower part, middle part and upper part of the reactor, contacting with the catalyst for preparation of dimethyl ether via methanol dehydration, carrying out the reaction of preparing dimethyl ether by methanol dehydration to obtain the reaction stream, separating said reaction stream to obtain a coked catalyst and a crude product primarily containing the target product, i.e. dimethyl ether; and (2) totally or partially feeding the coked catalyst obtained in step (1) into a regenerator in a continuous or batch manner for regeneration via coke-burning, the regenerated catalyst being directly recycled to step (1) after being totally or partially cooled.

Said methanol feedstock contains from 5 to 100 wt. %, preferably from 50 to 100 wt. %, more preferably from 90 to 100 wt. % of methanol, and may contain a small amount of impurities such as water the like. Said methanol feedstock is derived from crude methanol produced by gasification and synthesis from various fossil fuels, such as natural gas, coal, oil sand, petroleum oil and the like, or derived from other sources. Methanol in the present invention can be fed in a liquid phase, or in a gaseous phase after the heat exchange with the reaction product or other heat sources.

The reactor of the present invention comprises a riser reactor, a fluidized bed reactor, a composite riser+fluidized bed reactor, or other modified versions thereof, wherein said riser and fluidized bed may be isodiametric risers and fluidized beds, or various diameter-variable risers and fluidized beds.

The present invention preferably applies a composite riser (also referred to as "rising device")+fluidized bed reactor, wherein the reactor is arranged in a manner that the fluidized bed reactor is disposed at the top of the riser. Under the circumstance that a part of the coked catalyst is fed into the regenerator for regeneration via coke-burning in step (2), the remaining coked catalyst is cooled and recycled to the bottom of the reactor to re-participate in the reaction. At this time, a first catalyst mixing device may be disposed at the bottom of the riser. Due to such arrangement, the cooled coked catalyst can be quickly mixed with the regenerated catalyst from the regenerator, and the mixed catalyst and feedstock can be quickly risen to the fluidized bed reactor via the riser, so as to enable the temperature distribution and the catalyst activity distribution in the whole reactor to be more uniform than those in a single fluidized bed reactor. Meanwhile, since the catalyst and reactant stream in the riser move upward in an axial direction of the riser in a manner similar to piston flow and lead to less back-mixing, the use of the riser+fluidized bed reactor efficiently controls the reaction depth, so as to enable the dehydration reaction to more evenly release heat at different positions in the axial direction of the reactor and to have notable effect on increasing the single-pass conversion rate of methanol and the selectivity of dimethyl ether. Said methanol feedstock in step (1) is preferably fed from any two or more locations selected from the bottom of the first catalyst mixing device, the lower part of the riser, the middle part of the riser, the upper part of the riser, and the fluidized bed reactor, more preferably from said two to four locations.

The relative ratios of the methanol charging rate at different feeding locations should not be limited. During the multipoint feeding of the methanol material in step (1), nozzles, distributing pipe and/or distributing rings may be used.

The catalyst provided in the present invention comprises zeolite-type molecular sieves or/and non-zeolite-type molecular sieves. When the catalyst comprises both zeolite-type molecular sieves and non-zeolite-type molecular sieves, the weight ratio of said non-zeolite-type molecular sieves to zeolite-type molecular sieves ranges from 0.01 to 99, preferably from 0.02 to 98.

Said zeolite-type molecular sieve is one or more selected from the group consisting of zeolite-type molecular sieves having a large-pore structure and zeolite-type molecular sieves having a middle-pore structure.

Said zeolite-type molecular sieves having a large-pore structure are selected from the group consisting of FAU-structure zeolites, BETA-structure zeolites and modifiers thereof, wherein said FAU-structure zeolites are Y-series zeolites which is one or more selected from the group consisting of Y-type zeolites, HY zeolites, REY zeolites, REHY zeolites, USY zeolites, REUSY zeolites and modifiers thereof.

Said zeolite-type molecular sieves having a middle-pore structure are one or more selected from the group consisting of mordenites, ZSM-5 zeolites, ZSM-11 zeolites, ZSM-22 zeolites, ZSM-23 zeolites, ZSM-35 zeolites, ZSM-48 zeolites, ZSM-57 zeolites, ZRP zeolites and modifiers thereof.

Said non-zeolite-type molecular sieve is a silicoaluminophosphate molecular sieve, e.g. selected from one or more of SAPO-34, SAPO-11, SAPO-17, SAPO-41 and SAPO-44.

Said molecular sieve may be a commercially available product, or may be prepared by any of the current methods. In addition, said non-zeolite-type molecular sieve characterized with X-ray diffraction may be a silicoaluminophosphate molecular sieve at least comprising the diffraction peaks as shown in Table 1 before being calcined to remove the template agent, at least comprising the diffraction peaks as shown in Table 2 after being calcined to remove the template agent, and having the molar composition represented by anhydrous chemical formula in an oxide form, $Al_2O_3:yP_2O_5:zSiO_2$, wherein y ranges from 0.01 to 1.5 and z ranges from 0.05 to 50,

TABLE 1

| $2\theta(°)$ | d (Å) | Relative strength |
|---|---|---|
| 8.13-8.30 | 10.89-10.65 | VS |
| 11.55-11.72 | 7.66-7.55 | W |
| 14.17-14.35 | 6.25-6.17 | S |
| 16.43-16.61 | 5.39-5.34 | M |
| 18.34-18.52 | 4.84-4.79 | M |
| 20.16-20.34 | 4.40-4.36 | W |
| 21.79-21.99 | 4.08-4.04 | M |
| 23.30-23.50 | 3.82-3.78 | W |
| 24.74-24.94 | 3.60-3.57 | M-S |
| 26.12-26.32 | 3.41-3.39 | M-S |
| 28.69-28.89 | 3.11-3.09 | W-M |
| 29.88-30.08 | 2.99-2.97 | M |
| 32.14-32.44 | 2.78-2.76 | W-M |
| 35.33-35.63 | 2.54-2.52 | W |

TABLE 2

| $2\theta(°)$ | d (Å) | Relative strength |
|---|---|---|
| 8.21-8.31 | 10.77-10.63 | VS |
| 11.68-11.78 | 7.57-7.51 | W-M |
| 14.30-14.40 | 6.19-6.15 | S |
| 16.54-16.64 | 5.36-5.32 | W-M |
| 18.54-18.64 | 4.79-4.76 | M |
| 20.31-20.41 | 4.37-4.35 | W |
| 21.93-22.13 | 4.05-4.01 | W-M |
| 23.44-23.64 | 3.80-3.76 | W |
| 24.96-25.16 | 3.57-3.54 | M |
| 26.36-26.56 | 3.38-3.35 | M-S |
| 28.94-29.14 | 3.09-3.06 | W |
| 30.08-30.38 | 2.97-2.94 | M |
| 32.36-32.66 | 2.76-2.74 | W |
| 35.60-35.90 | 2.52-2.50 | W |

*W represents the relative strength of the diffraction peaks ranging from 0-20%; M represents the relative strength of the diffraction peaks ranging from 20-60%; S represents the relative strength of the diffraction peaks ranging from 60-80%; VS represents the relative strength of the diffraction peaks ranging from 80-100%; M-S represents the relative strength of the diffraction peaks ranging from 20-80%; W-M represents the relative strength of the diffraction peaks ranging from 0-60%.

Preferably, said y is from 0.1 to 1.4; and z is from 0.1 to 40. More preferably, said y is from 0.15 to 1.2; and z is from 0.2 to 20. Before being calcined to remove the template agent, said silicoaluminophosphate molecular sieve has the molar composition $xR:Al_2O_3:yP_2O_5:zSiO_2$ represented by anhydrous chemical formula in an oxide form, wherein R is an organic template agent in the molecular sieve crystal pore channel; x is from 0.01 to 5, preferably from 0.03 to 4; y is from 0.01 to 1.5; and z is from 0.05 to 50. Said organic template agent is one or more selected from the group consisting of diethylamine, di-n-propylamine, diisopropylamine and triethylamine. When said organic template agent is the mixture of diethylamine and di-n-propylamine, the molar composition of said silicoaluminophosphate molecular sieve before being calcined to remove the template agent is represented by the anhydrous chemical formula in an oxide form, $(x1R1+x2R2):Al_2O_3:yP_2O_5:zSiO_2$, wherein R1 and R2 are the template agents in the molecular sieve crystal pore channel, wherein R1 is diethylamine, and R2 is di-n-propylamine; x1+x2 is from 0.01 to 5, wherein either of x1 and x2 is not 0; y is from 0.01 to 1.5; and z is from 0.05 to 50. Preferably, x1+x2 are from 0.03 to 4.

The catalyst provided according to the present invention may comprise a matrix acting as a binder, diluent and support in the catalyst. Said matrix is optionally one or more selected from various heat resistant inorganic oxides commonly used as the catalyst support and/or matrix, e.g. one or more selected from the group consisting of alumina, silica, titanium oxide, magnesia, alumina-magnesia, silica-alumina, silica-magnesia, silica-zirconia, silica-thoria, silica-beryllia, silica-titanium oxide, silica-zirconia, titanium oxide-zirconia, silica-alumina-thoria, silica-alumina-titanium oxide, silica-alumina-magnesia, silica-alumina-zirconia, natural zeolite, synthetic zeolite molecular sieve, non-zeolite-type molecular sieve and clay, preferably one selected from synthetic zeolite molecular sieve, non-zeolite-type molecular sieve, silica, alumina and silica-alumina, or the compounds thereof. On the basis of the total weight of the catalyst, the content of said matrix components which are preferably one or more selected from alumina, silica and silica-alumina is not more than 95 wt %, preferably from 10 wt % to 90 wt %.

The catalyst provided according to the present invention may optionally comprises one or more metal components selected from the group consisting of non-aluminum metals from Group IIIA, metals from Group IVA, metals from Group VA, metals from Group IIB, metals from Group IVB, metals from Group VIB, metals from Group VIIB, metals from Group VIII and rare earth metals, preferably one or more selected from iron, gallium, germanium, tin, zirconium, copper, lead, zinc, cadmium, lanthanum, cerium, lanthanum-enriched mixed rare earth metals and cerium-enriched mixed rare earth metals. By weight of oxides and based on said catalyst, the content of said metal components is not more than 30 wt %, preferably not more than 10 wt %.

The reaction is carried out at a temperature from 100 to 550° C., preferably from 150 to 380° C., more preferably from 180 to 350° C., and at a pressure from 1 to 1500 kPa, preferably from 1 to 1000 kPa (the pressures in the present invention all refer to gauge pressures), wherein the weight ratio of the catalyst to alcohol feedstock (catalyst/alcohol ratio) is from 0.001 to 50, preferably from 0.005 to 40, and the total weight hourly space velocity is from 0.01 to 100 $h^{-1}$, preferably from 0.1 to 50 $h^{-1}$.

The part of coked catalyst which is sent to the coke-burning step accounts for 0.5 to 100% of total weight of the coked catalyst. Under the circumstance that a part of the coked catalyst is fed into the regenerator for regeneration via coke-burning, the remaining coked catalyst is cooled and recycled to the bottom of the reactor to re-participate in the reaction, wherein said part of the coked catalyst for regeneration accounts for 0.5 to 99% of total weight of the coked catalyst.

Said regeneration is a single-stage or two-stage regeneration, and said regenerated catalyst is a partially regenerated catalyst (i.e. semi-regenerated catalyst) or/and totally regenerated catalyst.

The part of the regenerated catalyst directly recycled to step (1) after being cooled accounts for 0.5 to 100% of total weight of the regenerated catalyst. While a part of the regenerated catalyst in step (2) is directly recycled to step (1), the other part of regenerated catalyst is cooled and then recycled to step (1) mixed with the fresh catalyst.

Said catalyst is one or more selected from the group consisting of the regenerated catalyst, fresh catalyst, semi-regenerated catalyst and coked catalyst.

The regenerated catalyst recycled to the reactor is cooled to a temperature from 100 to 650° C. via direct or indirect heat exchange. Direct heat exchange refers to heat exchange by directly contacting air having a lower temperature with the regenerated catalyst, wherein said air is the whole or partial of the air compressed with an air compressor and fed into the regenerator, i.e. preheating the air fed into the regenerator by using the high temperature heat energy of partial regenerated catalyst. Said direct heat exchanger is in a form of a fluidized bed or a riser, and the cooled catalyst separated by a cyclone separator is fed into the fluidized bed reactor after the impurity gases (nitrogen, oxygen, carbon dioxide and the like) are stripped with hot water vapour. Indirect heat exchange refers to the use of a heat exchanger, wherein the hot catalyst passes through the tube pass, and water vapour passes through the shell pass.

In the process of the present invention, since the dehydration of methanol is an exothermic reaction, and the temperature of the catalyst bed will increase, some means need to be taken to control the temperature increase of the catalyst bed in order to avoid the effect of the temperature increase on the dimethyl ether selectivity, wherein said means include increasing the catalyst replacement rate, multipoint feeding of methanol, releasing the heat emitted during the dehydration of methanol via a heat remover. Said heat remover may be a coil pipe disposed in the catalyst bed, wherein the feed methanol vapor, or water vapor may pass through the tube pass.

In the process of the present invention, methanol is dehydrated, and the reaction product is separated to obtain the gas product primarily containing dimethyl ether. Said gas product can be directly used as fuels such as civil liquefied gas and the like, or further separated to obtain dimethyl ether having a high purity as fine chemicals. The liquid phase product obtained by separation is recycled to the methanol dehydration reactor for further reaction.

According to the fluidized catalytic process for producing dimethyl ether from methanol, the reaction temperature of the catalyst bed can be efficiently controlled by controlling the feeding manner of the feedstock, the reaction conditions and selecting suitable reaction device and catalyst. Thus the heat released from such dehydration is more evenly distributed at different positions in the axial direction of the reactor, so as to avoid the occurrence of local high temperature in the reactor and of the deep dehydration reaction (e.g. production of low-carbon olefins) and to reduce carbon deposit on the catalyst and to prolong the service life of the catalyst. In addition, the process of the present invention can ensure large-scale production of dimethyl ether. Without prejudice to the present invention, the application of the process of the present invention by reference to the mature fluidized bed reaction technology can enable the yield of dimethyl ether in a single fluidized bed reactor to be more than 1000,000 ton/year, so that the process of the present invention is suitable for industrial application. In the present invention, the single-pass conversion of methanol is generally more than 80%, and the selectivity of dimethyl ether is more than 98%. Under preferred conditions, the single-pass conversion of methanol is as high as 84.72%, and the selectivity of dimethyl ether is as high as 99.25%.

MODE OF CARRYING OUT THE INVENTION

Figure 1:
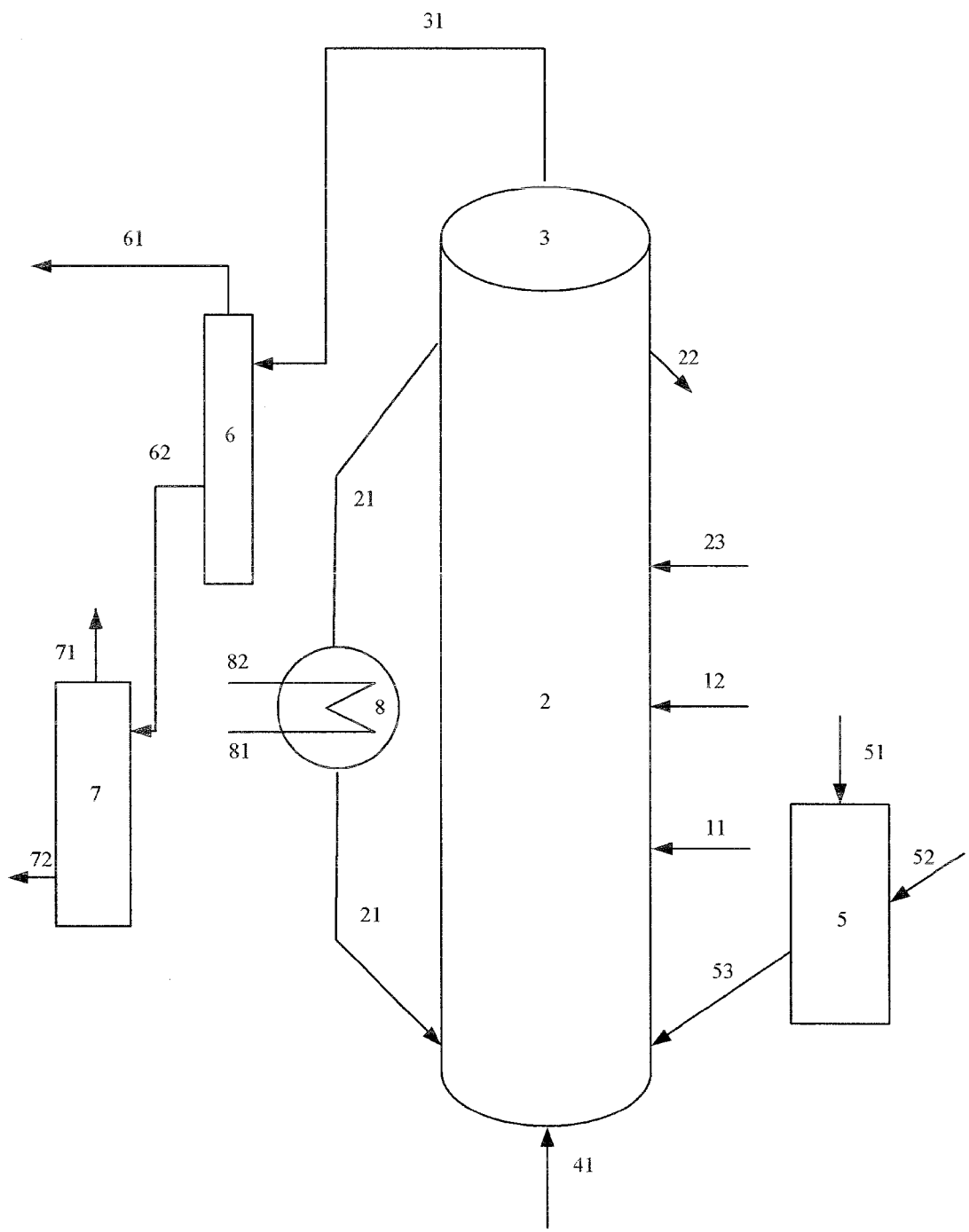
FIG. 1 and FIG. 2 are the flow schemes of the fluidized catalytic process for production of dimethyl ether via multiple-stage gaseous phase dehydration of methanol in the present invention.
Figure 2:
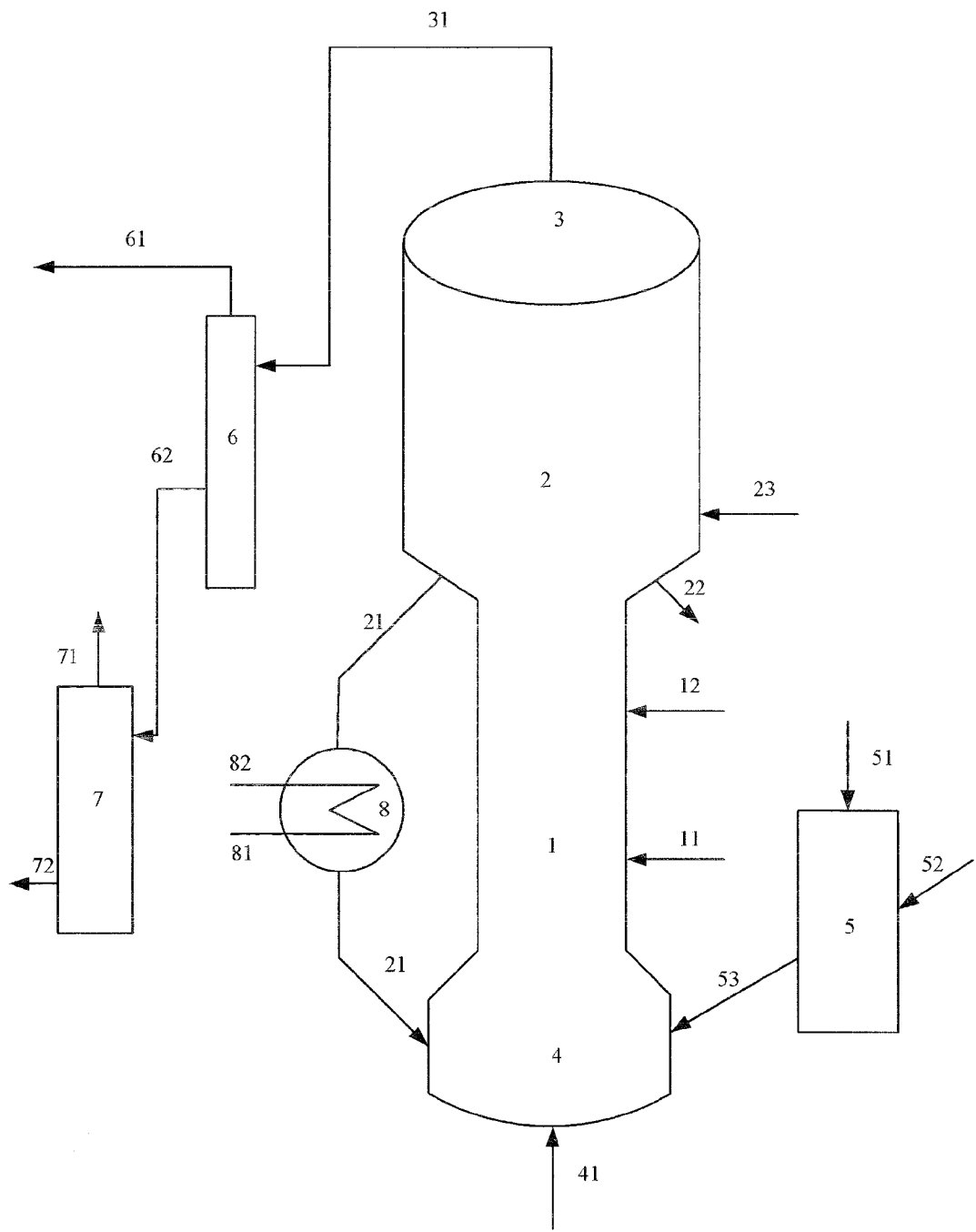

Further explanations are made for the process of the present invention by reference to FIG. 1 and FIG. 2, but are not used to limit the present invention.

The terms "top part", "bottom", "upper part", "middle part" and "lower part" herein all have the meanings well-known by those skilled in the art.

FIG. 1 shows the flow schemes of the fluidized catalytic process for production of dimethyl ether via the dehydration of methanol in gaseous phase by using a fluidized-bed reactor in the present invention. Reference sign 2 represents a fluidized-bed reactor; reference sign 3 represents a settling separator; reference sign 5 represents a second catalyst mixing device; reference sign 6 represents a first separation device; reference sign 7 represents a second separation device; reference sign 8 represents a heat exchange equipment; and other reference signs all represent pipelines.

In the process as shown in FIG. 1, the methanol feedstock, after heat exchange with the reactor effluents or the stream, e.g. hot catalyst, from the regeneration device, may be fed into the reactor in a four-point manner, wherein a part of the methanol feedstock is separately fed via the pipeline 41, or mixed with the inert gas and then fed to the bottom of the fluidized bed reactor 2; a part of the methanol feedstock is fed to the lower part of the fluidized bed reactor 2 via the pipeline 11; a part of the methanol feedstock is fed to the middle part of the fluidized bed reactor 2 via the pipeline 12; a part of the methanol feedstock is fed to the upper part of the fluidized bed reactor 2 via the pipeline 23. The temperature of the feed methanol at each inlets of the reactor is lower than the reaction temperature, usually from 20 to 350° C., preferably from 20 to 150° C., and more preferably from 40 to 100° C.

In the fluidized bed reactor, methanol is dehydrated at a temperature from 100 to 550° C., preferably from 150 to 380° C., more preferably from 180 to 350° C. and at a pressure from 1 to 1500 kPa, preferably from 1 to 1000 kPa (the pressures in the present invention all are gauge pressures), wherein the weight ratio of the catalyst to alcohol feedstock used in the reaction is from 0.001 to 50, preferably from 0.005 to 40; and the total weight hourly space velocity is from 0.01 to 100 $h^{-1}$, preferably from 0.1 to 50 $h^{-1}$. The reactant stream is separated by the settling separator 3 to obtain the crude product mainly comprising the target product dimethyl ether, and the coked catalyst, wherein the crude product mainly comprising the target product dimethyl ether leaves the reaction system via the pipeline 31. After being stripped and passing through the pipeline 21, a part of the stripped coked catalyst is cooled by the heat exchange equipment 8 and then is fed into the fluidized bed reactor 2. The cooling medium is fed into the coil pipe of the heat exchange equipment 8 via the pipeline 81, and discharged via the pipeline 82 after heat exchange with the catalyst, wherein the cooling medium may be methanol vapor or water vapor. Another part of the stripped coked catalyst is fed into the regenerator (which is not shown in the Figure) via the pipeline 22. The regenerated catalyst is fed into the second catalyst mixing device 5 via the pipeline 52, and fresh catalyst is fed into the second catalyst mixing device 5 via the pipeline 51. After being mixed, two catalysts are fed into the reactor 2 via the pipeline 53. The inert gas is fed into the reactor 2 via the pipeline 41 to mix the coked catalyst, fresh catalyst and/or the regenerated catalyst together, wherein the catalyst is in a fluidized state in the reactor. The inert gas may be one or more selected from the group consisting of water vapor, nitrogen and carbon dioxide.

After leaving the reaction system via the pipeline 31, the crude product mainly comprising the target product dimethyl ether is fed into the first separation device 6 and separated, wherein the separated gaseous phase product mainly comprising dimethyl ether is discharged via the pipeline 61, and the separated liquid phase product is fed into the second separation device 7 via the pipeline 62. After separation of the liquid phase product, a stream mainly comprising methanol is obtained and recycled via the pipeline 71 to the reactor 2 for further reaction; and the stream mainly comprising water is discharged from the second separation device 7 via the pipeline 72 for recycling.

FIG. 2 shows the flow schemes of the fluidized catalytic process for production of dimethyl ether via the dehydration of methanol in gaseous phase by using a riser+fluidized-bed reactor in the present invention. Reference sign 1 represents a riser; reference sign 2 represents a fluidized-bed reactor; reference sign 3 represents a settling separator; reference sign 4 represents a first catalyst mixing device; reference sign 5 represents a second catalyst mixing device; reference sign 6 represents a first separation device; reference sign 7 represents a second separation device; reference sign 8 represents a heat exchange equipment; and other reference signs all represent pipelines.

In the process as shown in FIG. 2, the methanol feedstock, after heat exchange with the reactor effluents or the stream, e.g. hot catalyst, from the regeneration device, may be fed into the reactor in a 4-point feeding manner, wherein a part of the methanol feedstock is separately fed via the pipeline 41, or mixed with the inert gas and then fed to the first catalyst mixing device 4; a part of the methanol feedstock is fed to the lower part of the riser via the pipeline 11; a part of the methanol feedstock is fed to the middle part of the riser via the pipeline 12; a part of the methanol feedstock is fed to the fluidized bed reactor 2 via the pipeline 23. The temperature of the feed methanol at each inlets of the reactor is lower than the reaction temperature, usually from 20 to 350° C., preferably from 20 to 150° C., and more preferably from 40 to 100° C.

The catalyst in the first catalyst mixing device 4 is risen to the fluidized bed reactor 2 by the riser 1. In the riser and fluidized bed reactor, methanol is dehydrated at a temperature from 100 to 550° C., preferably from 150 to 380° C., more preferably from 180 to 350° C. and at a pressure from 1 to 1500 kPa, preferably from 1 to 1000 kPa (the pressures in the present invention all are gauge pressures), wherein the weight ratio of the catalyst to alcohol feedstock used in the reaction is from 0.001 to 50, preferably from 0.005 to 40; and the total weight hourly space velocity is from 0.01 to 100 $h^{-1}$, preferably from 0.1 to 50 $h^{-1}$. The reactant stream is separated by the settling separator 3 to obtain the crude product mainly comprising the target product dimethyl ether, and the coked catalyst, wherein the crude product mainly comprising the target product dimethyl ether leaves the reaction system via the pipeline 31. After being stripped and passing through the pipeline 21, a part of the stripped coked catalyst is cooled by the heat exchange equipment 8 and then is fed into the first catalyst mixing device 4. The cooling medium is fed into the coil pipe of the heat exchange equipment 8 via the pipeline 81, and discharged via the pipeline 82 after heat exchange with the catalyst, wherein the cooling medium may be methanol vapor or water vapor. Another part of the stripped coked catalyst is fed into the regenerator (which is not shown in the Figure) via the pipeline 22. The regenerated catalyst is fed into the second catalyst mixing device 5 via the pipeline 52, and fresh catalyst is fed into the second catalyst mixing device 5 via the pipeline 51. After being mixed, two catalysts are fed into the first catalyst mixing device 4 via the pipeline 53. The inert gas is fed into the mixer via the pipeline 41 to mix the coked catalyst, fresh catalyst and/or the regenerated catalyst together, and the catalyst is pre-lifted to the bottom of the riser. The inert gas may be one or more selected from the group consisting of water vapor, nitrogen and carbon dioxide.

After leaving the reaction system via the pipeline 31, the crude product mainly comprising the target product dimethyl ether is fed into the first separation device 6 and separated, wherein the separated gaseous phase product mainly comprising dimethyl ether is discharged via the pipeline 61; and the separated liquid phase product is fed into the second separation device 7 via the pipeline 62. After separation of the liquid phase product, a stream mainly comprising methanol is obtained and recycled via the pipeline 71 to the reactor 2 for further reaction; and the stream mainly comprising water is discharged from the second separation device 7 via the pipeline 72 for recycling.

The following examples are used to further explain the presence process, but are not used to limit the present process.

EXAMPLE 1

This example illustrates a silicoaluminophosphate molecular sieve and the preparation thereof.

288.2 g of phosphoric acid (85% phosphoric acid, chemically pure reagent) and 905.2 g of deionized water were added into the gelling kettle in a water bath at 45° C., mixed and thoroughly stirred. After stirring for 30 min, 178.1 g of hydrated alumina (containing 72% $Al_2O_3$, produced by Changling Catalyst Factory) were added and stirred and mixed for 2 h. Then 145.0 g of diethylamine were added into said gelling kettle. After continuously stirred and mixed for 1 h, 288.5 g of silica sol were added. After thoroughly stirring, 15.8 g of SAPO-41 (produced by Changling Catalyst Factory) were added and sufficiently stirred for 2 h to produce a mixture. A part of the mixture was loaded into the stainless steel crystallization kettle, stirred and crystallized at 190° C. and the self-generated pressure for 80 h. The crystallized product was filtered, rinsed, and dried at 100-110° C. to obtain the molecular sieve powder product. A part of said crystallized product was taken out for the X-ray powder diffraction assay (the scanning range: $2\theta=5°-35°$), and the results were as shown in Table 3.

A part of said molecular sieve powder was taken out, and then heated up to a temperature of 550° C. at a temperature increasing rate of 2° C./min in an air atmosphere in a calcination furnace, maintained at this temperature for 3 h, then naturally cooled down to the room temperature in air. The calcined sample was taken out for the X-ray powder diffraction assay, and the results were as shown in Table 4. After calcination, a silicoaluminophosphate molecular sieve M-1 having the molar composition of $Al_2O_3:0.53P_2O_5:1.1SiO_2$ was obtained.

TABLE 3

| $2\theta(°)$ | d (Å) | Relative strength |
|---|---|---|
| 8.181 | 10.799 | 100.0 |
| 11.600 | 7.623 | 12.3 |
| 14.216 | 6.225 | 73.4 |
| 16.482 | 5.374 | 26.0 |
| 18.394 | 4.819 | 27.2 |
| 20.207 | 4.391 | 8.2 |
| 21.893 | 4.056 | 34.8 |
| 23.400 | 3.798 | 14.8 |
| 24.844 | 3.581 | 49.4 |
| 26.221 | 3.396 | 59.0 |
| 28.788 | 3.099 | 19.6 |
| 29.982 | 2.978 | 32.2 |
| 32.243 | 2.774 | 22.5 |

TABLE 3-continued

| $2\theta(°)$ | d (Å) | Relative strength |
|---|---|---|
| 33.306 | 2.693 | 3.2 |
| 35.418 | 2.534 | 18.2 |
| 40.283 | 2.238 | 3.2 |
| 42.085 | 2.146 | 5.1 |
| 43.830 | 2.065 | 7.4 |
| 47.143 | 1.927 | 8.1 |
| 47.925 | 1.898 | 8.0 |
| 48.726 | 1.868 | 5.4 |
| 49.534 | 1.840 | 3.2 |

TABLE 4

| $2\theta(°)$ | d (Å) | Relative strength |
|---|---|---|
| 8.264 | 10.696 | 100.0 |
| 11.727 | 7.544 | 34.1 |
| 14.346 | 6.172 | 79.5 |
| 16.593 | 5.341 | 21.6 |
| 18.591 | 4.771 | 21.0 |
| 20.357 | 4.361 | 1.1 |
| 22.029 | 4.034 | 21.4 |
| 23.544 | 3.778 | 15.9 |
| 25.058 | 3.553 | 45.7 |
| 26.463 | 3.367 | 61.4 |
| 29.042 | 3.074 | 16.6 |
| 30.234 | 2.955 | 33.5 |
| 32.505 | 2.754 | 20.5 |
| 33.585 | 2.668 | 3.6 |
| 35.710 | 2.514 | 16.0 |

EXAMPLE 2

This example illustrates a silicoaluminophosphate molecular sieve and the preparation thereof.

141.7 g of phosphoric acid (which was the same as that in Example 1) and 553 g of deionized water were added into the gelling kettle in a water bath at 45° C., mixed and thoroughly stirred. After stirring for 30 min, 116.5 g of hydrated alumina (which was the same as that in Example 1) were added and stirred and mixed for 2 h. Then 73.0 g of diethylamine and 81 g of di-n-propylamine were respectively added into said gelling kettle. After continuously stirred and mixed for 1 h, 153.8 g of silica sol (containing 26% $SiO_2$, produced by Beijing Changhong Chemical Plant) were added. After thoroughly stirring, 8 g of a silicoaluminophosphate molecular sieve having the AFO structure (synthesized according to the process disclosed in EP254075) were added and sufficiently stirred for 2 h to produce a mixture. A part of the mixture was loaded into the stainless steel crystallization kettle, stirred and crystallized at 190° C. and the self-generated pressure for 40 h. The crystallized product was filtered, rinsed, and dried at 100-110° C. to obtain the silicoaluminophosphate molecular sieve powder. A part of said silicoaluminophosphate molecular sieve powder was taken out for the X-ray powder diffraction assay (the scanning range: $2\theta=5°-35°$), and the results satisfied the characteristics in Table 1.

A part of said silicoaluminophosphate molecular sieve powder was taken out, heated up to a temperature of 550° C. at a temperature increasing rate of 2° C./min in an air atmosphere in a calcination furnace, maintained at this temperature for 3 h, then naturally cooled down to the room temperature in air. The calcined sample was taken out for the X-ray powder diffraction assay, and the results satisfied the characteristics in Table 2. The calcined silicoaluminophosphate molecular sieve was denominated as M-2 (having a solid content of 90 wt %) having the molar composition of $Al_2O_3:0.42P_2O_5:0.76SiO_2$.

Examples 3-5 illustrate the catalyst provided in the present invention and the preparation process thereof.

EXAMPLE 3

0.9 kg of halloysite (produced by Suzhou Kaolin Company and having a solid content of 74.0 wt %) were added into 6.0 Kg of decationized water, stirred for 1 h to sufficiently disperse kaolin. Then 60 ml of hydrochloric acid (produced by Beijing Chemical Works, chemically pure and having a concentration of from 36-38 wt %) and 0.7 kg of pseudo-boehmite (produced by Shandong Aluminums Factory, containing 61.0 wt % of $Al_2O_3$) were added, stirred for 1 h to dissolve pseudo-boehmite, heated up to a temperature of 60° C., maintaining for 1 h, and cooled down to room temperature.

0.3 Kg of REHY molecular sieve (produced by Qilu Catalyst Factory, having a solid content of 95.0 wt % and a $RE_2O_3$ content of 3.4 wt %) and 3.7 Kg of ZSM-5 molecular sieve (produced by Qilu Catalyst Factory, having a solid content of 85.0 wt %) were added into 6.8 Kg of decationized water. After sufficient dispersion by the homogenizer, the mixture was added into said pseudo-boehmite-clay slurry and stirred for 0.5 h. Then 3.6 Kg of alumina sol (produced by Qilu Catalyst Factory, having a $Al_2O_3$ concentration of 22.0 wt %) was added therein, continuously stirred for 0.5 h to obtain a catalyst slurry having a solid content of 26.2 wt % and a pH of 3.9.

Said slurry was spray dried and moulded at a tail gas temperature of 250° C., calcined at 650° C. for 2 h to obtain the microspheric catalyst MTD-1 consisting of 5 wt % of REHY, 57.3 wt % of ZSM-5 molecular sieves, 12.7% wt % of kaolin, and 25 wt % of $Al_2O_3$ binder.

EXAMPLE 4

96.8 g of $FeCl_3.6H_2O$ were dissolved in 3.6 Kg of decationized water. 3.7 Kg of ZSM-5 molecular sieves (produced by Qilu Catalyst Factory, having a solid content of 85.0 wt %) were added, impregnated, dried and calcined at 550° C. for 2 h to obtain Fe-modified ZSM-5 molecular sieves having a Fe content of 1.0 wt %.

1.4 L of sulfuric acid (produced by Beijing Chemical Works, chemically pure and having a concentration of 95-98 wt %) were diluted with 8.0 Kg of decationized water and cooled. 15.4 g of sodium water glass (commercially available, having a $SiO_2$ concentration of 26.0 wt % and a module of 3.2) were diluted with 8.5 Kg of decationized water. Under the condition of stirring, the diluted sodium water glass was slowly added into said diluted solution of sulfuric acid to obtain a silica sol having a $SiO_2$ concentration of 12.0 wt % and a pH of 1.5.

9.1 Kg of alumina sol (produced by Qilu Catalyst Factory, having a $Al_2O_3$ content of 22.0 wt %) were added into said silica sol and continuously stirred for 0.5 h. 0.3 Kg of M-1 and said Fe-modified ZSM-5 molecular sieves were added into 4.0 kg of decationized water. After sufficient dispersion by the homogenizer, the mixture was added into said pseudo-boehmite-clay slurry and stirred for 0.5 h to obtain a catalyst slurry having a solid content of 19.2 wt % and a pH of 2.8.

Said slurry was spray dried and moulded at a tail gas temperature of 250° C., calcined at 650° C. for 2 h to obtain the microspheric catalyst MTD-2 consisting of 30 wt % of M-1, 5 wt % of Fe-modified ZSM-5 molecular sieves, 40% wt % of $SiO_2$ binder, and 25 wt % of $Al_2O_3$ binder.

EXAMPLE 5

5.1 kg of halloysite (produced by Suzhou Kaolin Company and having a solid content of 74.0 wt %) were added into 16.0 Kg of decationized water, stirred for 1 h to sufficiently disperse kaolin. Then 400 ml of hydrochloric acid (produced by Beijing Chemical Works, chemically pure and having a concentration of from 36-38 wt %) and 6.6 kg of pseudo-boehmite (produced by Shandong Aluminums Factory, containing 61.0 wt % of $Al_2O_3$) were added, stirred for 1 h to dissolve pseudo-boehmite, heated up to a temperature of 60° C., maintaining for 1 h, and cooled down to room temperature.

0.7 Kg of M-1 molecular sieve and 2.8 Kg of DASY molecular sieve (produced by Qilu Catalyst Factory, having a solid content of 95.0 wt % and a $RE_2O_3$ content of 2.0 wt %) were added into 2.0 Kg of decationized water. After sufficient dispersion by the homogenizer, the mixture was added into said pseudo-boehmite-clay slurry and stirred for 0.5 h to obtain a catalyst slurry having a solid content of 20.9 wt % and a pH of 2.4.

Said slurry was spray dried and moulded at a tail gas temperature of 250° C., calcined at 650° C. for 2 h to obtain the microspheric catalyst MTD-3 consisting of 2 wt % of M-1, 8 wt % of DASY zeolites, 30 wt % of kaolin, and 49 wt % of $Al_2O_3$ binder.

Examples 6-9 showed the fluidized catalytic process for producing dimethyl ether by methanol dehydration using the catalyst provided in the present invention on a pilot-scale apparatus.

EXAMPLE 6

The methanol feedstock had a purity of 99.5 wt %, and the properties were as shown in Table 5. The code of the catalyst used in this example was MTD-1, and the reactor was a fluidized bed reactor.

80% of the methanol feedstock was fed into the fluidized bed reactor from the lower part of the reactor via the pipeline 11; and the remaining 20% of the methanol feedstock was mixed with the inert gas $N_2$ and fed into the reactor from the bottom of the reactor via the pipeline 41, and was in contact with MTD-1 catalyst.

Under the reaction conditions as stated in Table 6, the reactant stream was separated to obtain the coked catalyst and the crude product mainly comprising the target product dimethyl ether. Said crude product mainly comprising the target product dimethyl ether was further separated to obtain the target product dimethyl ether. The coked catalyst was divided into two parts, wherein 30 wt % of the coked catalyst was fed into the regenerator for regeneration via coke-burning, and the remaining 70 wt % of the coked catalyst was recycled to the lower part of the reactor. The product distribution was as shown in Table 6

After the coked catalyst in the regenerator was generated, it was divided into two parts, wherein one part was directly recycled to the lower part of the reactor after heat exchange, and the other part was mixed with fresh catalyst and recycled to the fluidized bed reactor.

Test results showed that the simultaneous feeding from the inlets at the bottom and the lower part of the reactor can maintain higher methanol conversion and dimethyl ether selectivity. Meanwhile, the reaction equipment required less additional fuels or other heat sources due to the heat release and/or heat exchange between the regenerated catalyst and reactor.

EXAMPLE 7

The methanol feedstock had a purity of 99.5 wt %, and the properties were as shown in Table 5. The code of the catalyst used in this example was MTD-1, and the reactor was a riser+fluidized bed.

80% of the methanol feedstock was fed into the fluidized bed reactor from the lower part of the riser via the pipeline 11; and the remaining 20% of the methanol feedstock was mixed with the inert gas $N_2$ and fed into the fluidized bed reactor from the bottom of the first catalyst mixing device via the pipeline 41, and was in contact with MTD-1 catalyst.

Under the reaction conditions as stated in Table 6, the reactant stream was separated to obtain the coked catalyst and the crude product mainly comprising the target product dimethyl ether. Said crude product mainly comprising the target product dimethyl ether was further separated to obtain the target product dimethyl ether, wherein the product distribution was as shown in Table 6. The coked catalyst was divided into two parts, wherein 30 wt % of the coked catalyst was fed into the regenerator for regeneration via coke-burning, and the remaining 70 wt % of the coked catalyst was recycled to the bottom of the first catalyst mixing device.

After the coked catalyst in the regenerator was generated, it was divided into two parts, wherein one part was directly recycled to the bottom of the first catalyst mixing device after heat exchange, and the other part was mixed with fresh catalyst and recycled to the fluidized bed reactor via the first catalyst mixing device and the riser in turn.

Test results showed that, as compared with Example 6 in which only the fluidized bed reactor was used, the simultaneous feeding of the methanol feedstock from the inlets at the lower part of the riser and at the bottom of the first catalyst mixing device can achieve higher methanol conversion and dimethyl ether selectivity. Meanwhile, the reaction equipment required less additional fuels or other heat sources due to the heat release and/or heat exchange between the regenerated catalyst and reactor.

EXAMPLE 8

The methanol feedstock had a purity of 99.5 wt %, and the properties were as shown in Table 5. The code of the catalyst used in this example was MTD-2, and the reactor was a riser+fluidized bed.

80% of the methanol feedstock was fed into the fluidized bed reactor from the lower part of the riser via the pipeline 11; and the remaining 20% of the methanol feedstock was mixed with the inert gas $N_2$ and fed into the fluidized bed reactor from the bottom of the first catalyst mixing device via the pipeline 41, and was in contact with MTD-2 catalyst.

Under the reaction conditions as stated in Table 6, the reactant stream was separated to obtain the coked catalyst and the crude product mainly comprising the target product dimethyl ether. Said crude product mainly comprising the target product dimethyl ether was further separated to obtain the target product dimethyl ether, wherein the product distribution was as shown in Table 6. The coked catalyst was divided into two parts, wherein 30 wt % of the coked catalyst was fed into the regenerator for regeneration via coke-burning, and the remaining 70 wt % of the coked catalyst was recycled to the bottom of the first catalyst mixing device.

After the coked catalyst in the regenerator was generated, it was divided into two parts, wherein one part was directly recycled to the bottom of the first catalyst mixing device after heat exchange, and the other part was mixed with fresh catalyst and recycled to the fluidized bed reactor via the first catalyst mixing device and the riser in turn.

Test results showed that, as compared with Example 6 in which only the fluidized bed reactor was used, the simultaneous feeding of the methanol feedstock from the inlets at the bottom of the riser and at the bottom of the first catalyst mixing device can obtain higher methanol conversion and dimethyl ether selectivity. Meanwhile, the reaction equipment required less additional fuels or other heat sources due to the heat release and/or heat exchange between the regenerated catalyst and reactor.

EXAMPLE 9

The methanol feedstock had a purity of 99.5 wt %, and the properties were as shown in Table 5. The code of the catalyst used in this example was MTD-3, and the reactor was a riser+fluidized bed.

The methanol feedstock was fed in a four-point manner, wherein 20% of the methanol feedstock was fed into the fluidized bed reactor from the lower part of the riser via the pipeline 11; 10% of the methanol feedstock was fed into the fluidized bed reactor from the middle part of the riser via the pipeline 12; 10% of the methanol feedstock was mixed with the inert gas $N_2$ and fed into the fluidized bed reactor from the bottom of the first catalyst mixing device via the pipeline 41; and 60% of the methanol feedstock was fed into the fluidized bed reactor via the pipeline 23 and was in contact with MTD-3 catalyst.

Under the reaction conditions as stated in Table 6, the reactant stream was separated to obtain the coked catalyst and the crude product mainly comprising the target product dimethyl ether. Said crude product mainly comprising the target product dimethyl ether was further separated to obtain the target product dimethyl ether, wherein the product distribution was as shown in Table 6. The coked catalyst was divided into two parts, wherein 20 wt % of the coked catalyst was fed into the regenerator for regeneration via coke-burning, and the remaining 80 wt % of the coked catalyst was recycled to the bottom of the first catalyst mixing device.

After the coked catalyst in the regenerator was generated, it was divided into two parts, wherein one part was directly recycled to the bottom of the first catalyst mixing device after heat exchange, and the other part was mixed with fresh catalyst and recycled to the fluidized bed reactor via the first catalyst mixing device and the riser in turn. The total weight of said the other part and fresh catalyst was equivalent to 20 wt % of the coked catalyst.

Test results showed that the methanol feedstock was fed in a four-point manner, wherein a part of the methanol feedstock was fed at the bottom of the riser; a part of the methanol feedstock was fed at the middle part of the riser; a part of the methanol feedstock was fed at the bottom of the first catalyst mixing device; and a part of the methanol feedstock was directly fed from the fluidized bed layer, so as to control the temperature of the catalyst bed to the greatest extent and to obtain the optimal methanol conversion and dimethyl ether selectivity. Meanwhile, the reaction equipment required less additional fuels or other heat sources due to the heat release and/or heat exchange between the regenerated catalyst and reactor.

COMPARISON EXAMPLE 1

The methanol feedstock had a purity of 99.5 wt %, and the properties were as shown in Table 5. The code of the catalyst used in this comparison example was MTD-1, and the reactor was a fluidized bed reactor.

The methanol feedstock was merely fed into the fluidized bed reactor from the lower part of the reactor via the pipeline 11, and was in contact with MTD-1 catalyst. The pipeline 41 was merely used for conveying $N_2$. Under the reaction conditions as stated in Table 7, the reactant stream was separated to obtain the coked catalyst and the crude product mainly comprising the target product dimethyl ether. Said crude product mainly comprising the target product dimethyl ether was further separated to obtain the target product dimethyl ether, wherein the product distribution was as shown in Table 7. The coked catalyst was divided into two parts, wherein 30 wt % of the coked catalyst was fed into the regenerator for regeneration via coke-burning, and the remaining 70 wt % of the coked catalyst was recycled to the bottom of the first catalyst mixing device.

After the coked catalyst in the regenerator was generated, it was divided into two parts, wherein one part was directly recycled to the fluidized bed reactor after heat exchange, and the other part was mixed with fresh catalyst and recycled to the fluidized bed reactor.

Test results showed that, when the methanol feedstock was fed only from the inlet at the lower part of the fluidized bed, both the methanol conversion and selectivity of dimethyl ether under the same reaction conditions were significantly lower than those in Example 6.

COMPARISON EXAMPLE 2

The methanol feedstock had a purity of 99.5 wt %, and the properties were as shown in Table 5. The code of the catalyst used in this comparison example was MTD-1, and the reactor was a riser+fluidized bed.

The methanol feedstock was merely fed into the fluidized bed reactor from the lower part of the riser via the pipeline 11, and was in contact with MTD-1 catalyst. The pipeline 41 was merely used for conveying $N_2$. Under the reaction conditions as stated in Table 7, the reactant stream was separated to obtain the coked catalyst and the crude product mainly comprising the target product dimethyl ether. Said crude product mainly comprising the target product dimethyl ether was further separated to obtain the target product dimethyl ether, wherein the product distribution was as shown in Table 7. The coked catalyst was divided into two parts, wherein 30 wt % of the coked catalyst was fed into the regenerator for regeneration via coke-burning, and the remaining 70 wt % of the coked catalyst was recycled to the bottom of the first catalyst mixing device.

After the coked catalyst in the regenerator was generated, it was divided into two parts, wherein one part was directly recycled to the fluidized bed reactor after heat exchange, and the other part was mixed with fresh catalyst and recycled to the fluidized bed reactor. The total weight of said the other part and fresh catalyst was equivalent to 30 wt % of the coked catalyst.

Test results showed that, when the methanol feedstock was fed only from the inlet at the bottom of the riser, both the methanol conversion and selectivity of dimethyl ether under the same reaction conditions were significantly lower than those in Example 7.

TABLE 5

| Properties of the raw materials | Methanol |
|---|---|
| Purity, % | analytically pure >99.5 |
| Density (20° C.), g/cm³ | 0.791~0.793 |
| Water content, % | 0.1 |
| Acidity (by weight of $H^+$), mmol/100 g | 0.04 |
| Evaporation residue, % | 0.001 |

TABLE 6

| Catalyst | Example 6 MTD-1 | Example 7 MTD-1 | Example 8 MTD-2 | Example 9 MTD-3 |
|---|---|---|---|---|
| Reaction conditions for catalytic conversion of methanol | | | | |
| Temperature, ° C. | 280 | 280 | 180 | 360 |
| Pressure (gauge pressure), MPa | 0.1 | 0.1 | 0.4 | 0.1 |
| Catalyst-to-alcohol ratio | 2.5 | 2.5 | 2.5 | 2.5 |
| Weight hourly space velocity, $h^{-1}$ | 3.0 | 3.0 | 0.5 | 3.0 |
| Product distribution, m % | | | | |
| Dimethyl ether | 56.10 | 57.62 | 46.66 | 57.86 |
| Light hydrocarbons | 0.65 | 0.64 | 0.21 | 1.99 |
| Water | 24.15 | 24.84 | 20.94 | 25.26 |
| Coke | 0.32 | 0.31 | 0.1 | 0.95 |
| Unconverted methanol | 18.78 | 16.59 | 32.08 | 13.94 |
| Methanol conversion rate, % | 81.22 | 83.41 | 67.92 | 86.06 |
| Selectivity of dimethyl ether, % | 99.01 | 98.96 | 99.81 | 96.78 |

TABLE 7

| Catalyst | Comp. Exp. 1 MTD-1 | Comp. Exp. 2 MTD-1 |
|---|---|---|
| Reaction conditions for catalytic conversion of methanol | | |
| Temperature, ° C. | 280 | 280 |
| Pressure (gauge pressure), MPa | 0.1 | 0.1 |
| Catalyst-to-alcohol ratio | 2.5 | 2.5 |
| Weight hourly space velocity, $h^{-1}$ | 3.0 | 3.0 |
| Product distribution, m % | | |
| Dimethyl ether | 51.53 | 53.67 |
| Light hydrocarbons | 0.71 | 0.62 |
| Water | 22.41 | 23.38 |
| Coke | 0.80 | 0.75 |
| Unconverted methanol | 24.55 | 21.58 |
| Methanol conversion rate, % | 75.45 | 78.42 |
| Selectivity of dimethyl ether, % | 98.67 | 98.86 |

Although some preferred examples are used above to explain the present invention, it is understandable that these examples are intended for explanation, rather than for limiting the scope of the present invention.

What is claimed is:

1. A fluidized catalytic process for production of dimethyl ether from methanol, wherein said process is carried out in a reactor in which the catalyst is in a fluidized state, characterized in that said process comprises the following steps of
(1) feeding the methanol feedstock via two or more locations selected from the bottom, lower part, middle part and upper part of the reactor, contacting with the catalyst for preparation of dimethyl ether via methanol dehydration, carrying out the reaction of preparing dimethyl ether by methanol dehydration to obtain the reaction stream, separating said reaction stream to obtain a coked catalyst and a crude product primarily containing the target product, i.e., dimethyl ether; and (2) totally or partially feeding the coked catalyst obtained in step (1) into a regenerator in a continuous or batch manner for regeneration via coke-burning, the regenerated catalyst being directly recycled to step (1) after being totally or partially cooled;

characterized in that said reactor is a composite riser+fluidized bed reactor, wherein said fluidized bed reactor is located at the top of the riser, and a first catalyst mixing device is set up at the bottom of said riser, and characterized in that said methanol feedstock is fed via two or more locations selected from the bottom of the first catalyst mixing device, the lower part of the riser, the middle part of the riser, the upper part of the riser, and the fluidized bed reactor, wherein at least one of said methanol feedstock feed locations is to the fluidized bed reactor.

2. The process according to claim 1, characterized in that said methanol is fed via two to four locations selected from the bottom of the first catalyst mixing device, the lower part of the riser, the middle part of the riser, the upper part of the riser, and the fluidized bed reactor bed.

3. The process according to claim 1, characterized in that said methanol feedstock contains from 5 to 100 wt. % of methanol.

4. The process according to claim 1, characterized in that said methanol feedstock contains from 50 to 100 wt. % of methanol.

5. The process according to claim 1, characterized in that said methanol feedstock contains from 90 to 100 wt. % of methanol.

6. The process according to claim 1, characterized in that said methanol is fed in a liquid phase or a gaseous phase.

7. The process according to claim 1, characterized in that said catalyst comprises at least one zeolite-type molecular sieve, or at least one non-zeolite-type molecular sieve, or combination thereof.

8. The process according to claim 1, characterized in that said catalyst comprise at least one zeolite-type molecular sieve.

9. The process according to claim 7, characterized in that said zeolite-type molecular sieve is one or more selected from the group consisting of zeolite-type molecular sieves having a large-pore structure and zeolite-type molecular sieves having a middle-pore structure, wherein the zeolite-type molecular sieves having a large-pore structure are one or more selected from the group consisting of FAU-structure zeolites, BETA-structure zeolites and modifiers thereof, wherein said FAU-structure zeolites are Y-series zeolites which is one or more selected from the group consisting of Y-type zeolites, HY zeolites, REY zeolites, REHY zeolites, USY zeolites, REUSY zeolites and modifiers thereof; the zeolite-type molecular sieves having a middle-pore structure are one or more selected from the group consisting of mordenites, ZSM-5 zeolites, ZSM-11 zeolites, ZSM-22 zeolites, ZSM-23 zeolites, ZSM-35 zeolites, ZSM-48 zeolites, ZSM-57 zeolites, ZRP zeolites and modifiers thereof.

10. The process according to claim 7, characterized in that said non-zeolite-type molecular sieve is a silicoaluminophosphate molecular sieve selected from one or more of SAPO-34, SAPO-11, SAPO-17, SAPO-41 and SAPO-44.

11. The process according to claim 7, characterized in that said non-zeolite-type molecular sieve characterized with X-ray diffraction is a silicoaluminophosphate molecular sieve at least comprising the diffraction peaks as shown in Table 1 before being calcined to remove the template agent, at least comprising the diffraction peaks as shown in Table 2 after being calcined to remove the template agent, and having the molar composition represented by anhydrous chemical formula in an oxide form, $Al_2O_3:yP_2O_5:zSiO_2$, wherein y ranges from 0.01 to 1.5 and z ranges from 0.05 to 50,

TABLE 1

| 2θ(°) | d (Å) | Relative strength |
|---|---|---|
| 8.13-8.30 | 10.89-10.65 | VS |
| 11.55-11.72 | 7.66-7.55 | W |
| 14.17-14.35 | 6.25-6.17 | S |
| 16.43-16.61 | 5.39-5.34 | M |
| 18.34-18.52 | 4.84-4.79 | M |
| 20.16-20.34 | 4.40-4.36 | W |
| 21.79-21.99 | 4.08-4.04 | M |
| 23.30-23.50 | 3.82-3.78 | W |
| 24.74-24.94 | 3.60-3.57 | M-S |
| 26.12-26.32 | 3.41-3.39 | M-S |
| 28.69-28.89 | 3.11-3.09 | W-M |
| 29.88-30.08 | 2.99-2.97 | M |
| 32.14-32.44 | 2.78-2.76 | W-M |
| 35.33-35.63 | 2.54-2.52 | W |

TABLE 2

| 2θ(°) | d (Å) | Relative strength |
|---|---|---|
| 8.21-8.31 | 10.77-10.63 | VS |
| 11.68-11.78 | 7.57-7.51 | W-M |
| 14.30-14.40 | 6.19-6.15 | S |
| 16.54-16.64 | 5.36-5.32 | W-M |
| 18.54-18.64 | 4.79-4.76 | M |
| 20.31-20.41 | 4.37-4.35 | W |
| 21.93-22.13 | 4.05-4.01 | W-M |
| 23.44-23.64 | 3.80-3.76 | W |
| 24.96-25.16 | 3.57-3.54 | M |
| 26.36-26.56 | 3.38-3.35 | M-S |
| 28.94-29.14 | 3.09-3.06 | W |
| 30.08-30.38 | 2.97-2.94 | M |
| 32.36-32.66 | 2.76-2.74 | W |
| 35.60-35.90 | 2.52-2.50 | W. |

12. The process according to claim 1, characterized in that the part of coked catalyst which is sent to the coke-burning step accounts for 0.5 to 100% of total coked catalyst in weight.

13. The process according to claim 1, characterized in that, under the circumstance that a part of coked catalyst is fed into the regenerator for regeneration via coke-burning, the remaining coked catalyst is cooled and recycled to the bottom of the reactor to re-participate in the reaction, wherein said part of the coked catalyst for regeneration accounts for 0.5 to 99% of total coked catalyst in weight.

14. The process according to claim 1, characterized in that the part of regenerated catalyst directly recycled to step (1) after being cooled accounts for 0.5 to 100% of total regenerated catalyst in weight.

15. The process according to claim 1, characterized in that, while a part of the regenerated catalyst in step (2) is directly recycled to step (1), the other part of the regenerated catalyst is cooled and then recycled to step (1) mixed with fresh catalyst.

16. The process according to claim 1, characterized in that the regenerated catalyst recycled to the reactor is cooled to 100-650° C. via direct or indirect heat exchange.

17. The process according to claim 1, characterized in that the reaction is carried out at a temperature from 100 to 550° C., a pressure from 1 to 1500 kPa, a weight ratio from 0.001 to 50 of the catalyst to alcohol feedstock, and a total weight hourly space velocity from 0.1 to 100 h$^{-1}$.

18. The process according to claim 1, characterized in that the reaction is carried out at a temperature from 150 to 380° C., a pressure from 1 to 1000 kPa, a weight ratio from 0.005 to 40 of the catalyst to alcohol feedstock, and a total weight hourly space velocity from 0.1 to 50 h$^{-1}$.

19. The process according to claim 1, characterized in that the reaction is carried out at a temperature from 180 to 350° C., a pressure from 1 to 1000 kPa, a weight ratio from 0.005 to 40 of the catalyst to alcohol feedstock, and a total weight hourly space velocity from 0.1 to 50 h$^{-1}$.

* * * * *